US00RE34633E

United States Patent [19]

Sos et al.

[11] E Patent Number: Re. 34,633

[45] Reissued Date of Patent: Jun. 7, 1994

[54] BALLOON GUIDE

[75] Inventors: Thomas A. Sos, New Rochelle, N.Y.; Michael DeBruyne; Thomas A. Osborne, both of Bloomington, Ind.

[73] Assignee: Cook Incorporated, Bloomington, Ind.

[21] Appl. No.: 8,415

[22] Filed: Jan. 25, 1993

Related U.S. Patent Documents

Reissue of:

[64] Patent No.: 4,848,344
Issued: Jul. 18, 1989
Appl. No.: 120,463
Filed: Nov. 13, 1987

U.S. Applications:

[63] Continuation of Ser. No. 731,195, Jul. 15, 1991, abandoned.

[51] Int. Cl.[5] ..... A61M 29/02

[52] U.S. Cl. ..... 128/772; 606/194; 604/96

[58] Field of Search ..... 128/656–658, 128/772; 606/192, 194; 600/18; 604/95–103

[56] References Cited

U.S. PATENT DOCUMENTS

| | | | |
|---|---|---|---|
| 3,402,717 | 9/1968 | Doherty | 604/99 |
| 4,261,339 | 4/1981 | Hanson | 600/18 |
| 4,276,874 | 7/1981 | Wolvek | 600/18 |
| 4,467,790 | 8/1984 | Schiff | 600/18 |
| 4,540,404 | 9/1985 | Wolvek | 604/164 X |
| 4,545,390 | 10/1985 | Leary | 604/96 X |
| 4,561,439 | 12/1985 | Bishop | 606/194 |
| 4,641,654 | 2/1987 | Samson et al. | 604/100 X |
| 4,646,742 | 3/1987 | Packard et al. | 606/194 |
| 4,723,936 | 2/1988 | Buchbinder et al. | 604/96 X |
| 4,813,934 | 3/1989 | Engelson et al. | 604/99 |

*Primary Examiner*—Michael H. Thaler
*Attorney, Agent, or Firm*—Woodard, Emhardt, Naughton, Moriarty & McNett

[57] ABSTRACT

A balloon guide is disclosed which includes a single lumen useful alternately for fluid communication through the distal tip or for inflation of a balloon when the distal end is closed. The guide includes a body formed from coiled wire having a proximal portion in which the coils are held together and a distal portion in which the coils are separable. The balloon is located about the separable coils. A restriction adjacent the distal tip of the guide body is closable by a plug mandril extending through the central lumen of the guide. With the distal tip open, fluid communication is available through the central lumen for pressure measurements, fluid infusion or the like. In an alternate condition, a plug is positioned to close off the distal opening of the guide and also to stretch the coiled wire to separate the coils in the region underlying the balloon, preventing fluid communication through the distal tip, but permitting inflation or deflation of the balloon through the separated wire coils.

30 Claims, 2 Drawing Sheets

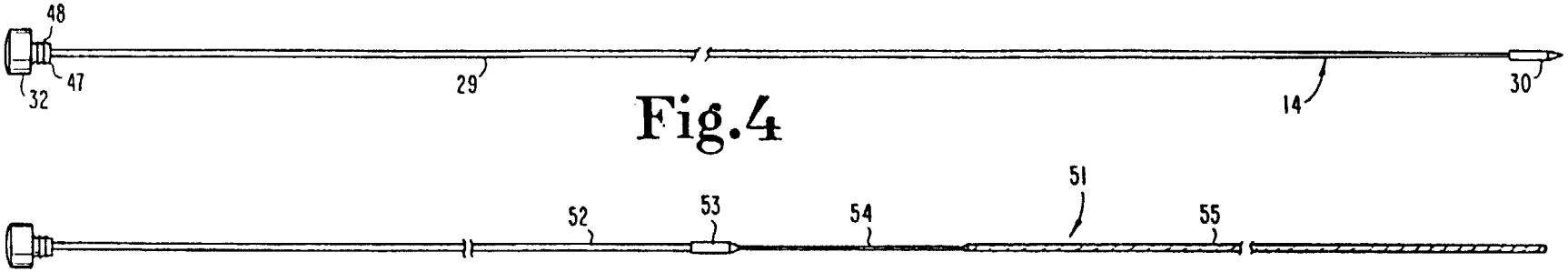
Fig.4
Fig.7
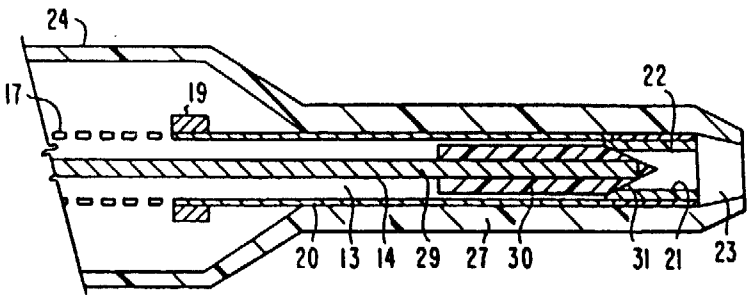
Fig.5
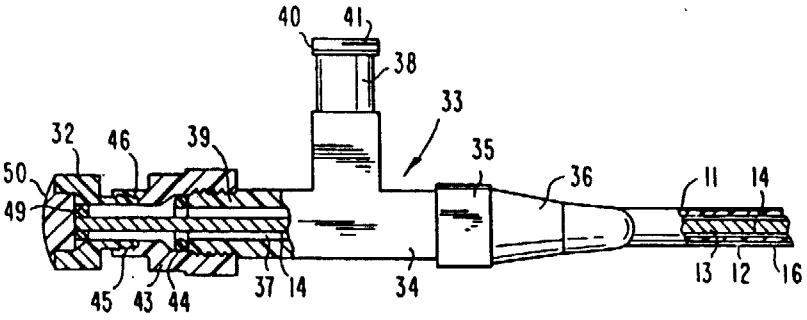
Fig.6

BALLOON GUIDE

Matter enclosed in heavy brackets [ ] appears in the original patent but forms no part of this reissue specification; matter printed in italics indicates the additions made by reissue.

*This application is a continuation of application No. 07/731,195, filed Jul. 15, 1991, now abandoned.*

BACKGROUND OF THE INVENTION

1. Field of the Invention

The present invention relates to the field of wire guides having an inflatable balloon adjacent the distal tip, and more particularly to a guide, such as an infusion guide, having a central lumen useful for both fluid communication through the distal tip and also for inflation of the balloon.

2. Description of the Prior Art

A great variety of wire guides have been known in the prior art for addressing particular applications. In many instances, it is desirable that a wire guide be readily advanced and maneuvered through the vascular system and out into the small, distal arteries and vessels with good efficiency. Some applications require the presence of an inflatable balloon adjacent the distal tip of the wire guide, such as in the performing of coronary angioplasties.

Standard coronary balloon angioplasty catheters of the prior art have employed two lumens to separately perform the roles of fluid communication and balloon inflation. In one embodiment, the prior art catheters have comprised a two lumen extruded tube, while other embodiments have used two single lumen extruded tubes extending coaxially. For the two lumen tube, the balloon is assembled to the catheter as a separate assembly. On the coaxial construction, the balloon is formed on the distal end of the outer tube and the annular space between the tubes becomes the inflation channel for the balloon.

Since these prior art catheters have used two separate lumens through the length of the catheter, there have been limitations regarding size. The inflation channel to the balloon needs to be as large as possible to decrease the length of time required to inflate and deflate the balloon. The balloon needs to inflate and deflate quickly because blood flow out into the heart muscle is stopped during the dilating process. The main or central lumen also needs to be as large as possible to allow good pressure measurements, the injection of radiopaque liquids in large enough quantities to produce useful X-ray visualization, and to allow the passage of various sized guide wires. The outside diameter for a coronary balloon catheter is limited to about 4 French (0.054 inches). Consequently, the two lumens used in the prior art catheters need to be fairly small. The inflation lumen of prior art catheters has measured in the range of 0.010 inches to 0.018 inches. The central lumen of prior art catheters has measured in the range of 0.018 inches to 0.021 inches in diameter.

A thrombectomy catheter or gallstone dislodger is described in U.S. Pat. No. 4,561,439 issued to Bishop, et al. on Dec. 31, 1985. The Bishop catheter has a closed, distal end, and includes a spring portion near the distal end. A balloon is attached about the spring portion, and the introduction of fluid into the lumen causes the spring to extend and the balloon to fill.

An elongatable balloon catheter is described in U.S. Pat. No. 4,276,874 issued to Wolvek, et al. on July 7, 1981. The Wolvek catheter includes an extendable, helical coil portion adjacent the distal, closed end. A balloon is secured about the coil portion. A rod extended through the central lumen of the catheter is used to extend the coil portion and thereby stretches the balloon to reduce the outside diameter of the balloon to facilitate movement of the catheter through a passageway.

Several other patents in the prior art have provided a variety of features in association with a balloon catheter. In U.S. Pat. No. 4,467,790 issued to Schiff on Aug. 28, 1984, there is disclosed a percutaneous balloon catheter which includes a balloon at the distal tip. A stylet extends through the balloon and is secured to the distal tip and upon rotation is used to wrap and unwrap the balloon to facilitate the percutaneous insertion of the catheter. A similar balloon catheter having a rotatable support for twisting and untwisting the balloon is shown in U.S. Pat. No. 4,261,339 issued to Hanson, et al. on Apr. 4, 1981.

A steerable guide wire for a balloon dilatation procedure is described in U.S. Pat. No. 4,545,390 issued to Leary on Oct. 8, 1985. The Leary device includes a balloon which is positioned in the region surrounding a coiled wire portion of the guide wire, but the balloon is inflated by means of a separate inflation lumen. In U.S. Pat. No. 4,540,404 issued to Wolvek on Sept. 10, 1985 there is described a balloon catheter which includes a movable sheath which is positioned over the balloon during insertion and then removed from the balloon for inflation.

There has remained a need for a balloon guide which can serve dual purposes in providing a fluid communicating lumen and also an inflatable balloon. The need has also remained for a balloon guide of this type which is a single lumen device that is able to perform two functions through one lumen and which achieves the advantages of a smaller outside diameter with a relatively larger inflation lumen.

SUMMARY OF THE INVENTION

Briefly describing one aspect of the present invention, there is provided a balloon guide which includes a guide body comprising a coiled wire having a first, proximal portion in which the coils are inseparable and a second, distal portion in which the coils are normally adjacent, but are separable, the guide body including a plug seat distal of the second wire portion and a balloon surrounding the second wire portion and inflatable therethrough, a plug mandril including an elongated mandril and a plug secured to the distal end for being received within and closing off the plug seat, means for extending the plug mandril into and through the central lumen and between a first position with the plug spaced from the plug seat and a second position locating the plug in sealing position against the plug seat and causing separation of the normally adjacent coils of the second portion of the coiled wire, and means for introducing a fluid into the central lumen and through the separated coils to inflate the balloon. In another aspect of the present invention, there is provided a method for inflating a balloon guide as disclosed.

It is an object of the present invention to provide a balloon guide which includes a central lumen for fluid communication through the distal end of the guide as well as an inflatable balloon adjacent the distal tip.

Another object of the present invention is to provide a balloon guide which is a single lumen device capable of both fluid communication and balloon inflation.

It is a further object of the present invention to provide a balloon guide that has a desirably small outside diameter and suitably large inflation lumen.

It is also an object of the present invention to provide a method for operating a single lumen device to be useful either for fluid communication through the distal end of the catheter or for inflation of a balloon.

Further objects and advantages of the present invention will become apparent from the description of the preferred embodiment which follows.

BRIEF DESCRIPTION OF THE DRAWINGS

FIG. 4 is a side, elevational view of a plug mandril useful with the present invention.

FIG. 5 is a partial, cross-sectional view of the distal end of the balloon guide of the present invention, and particularly showing the plug mandril seated in position to close off the distal end of the balloon guide.

FIG. 6 is a partial, cross-sectional view of a fitting useful with the present invention, and particularly adapted for locking the plug mandril in a desired position relative the balloon guide and permitting fluid communication with the central lumen of the balloon guide to facilitate inflation of the balloon.

FIG. 7 is a side, elevational view showing an alternate design for a plug mandril useful with the present invention.

DESCRIPTION OF THE PREFERRED EMBODIMENT

Figure 1:
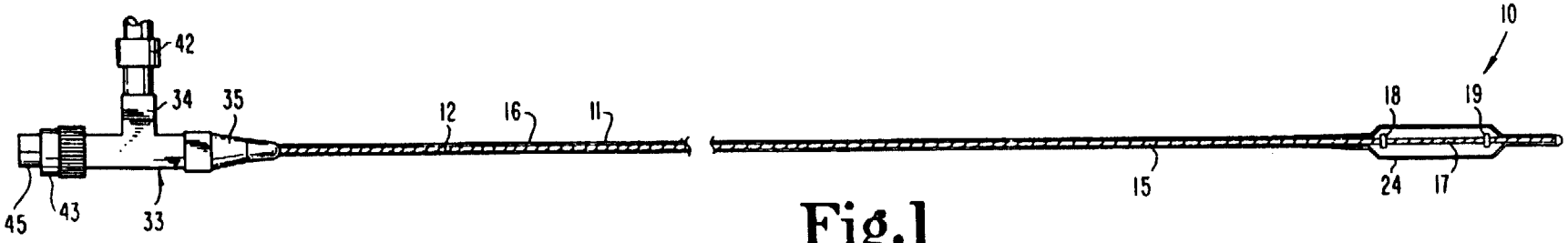
FIG. 1 is a side, elevational view of a balloon guide constructed in accordance with a preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
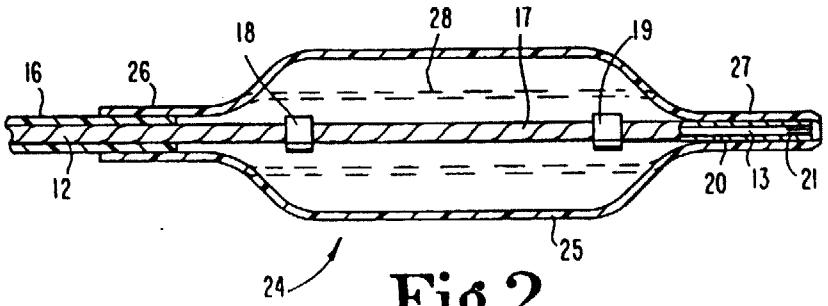
FIG. 2 is a partial, cross-sectional view of the distal end of the balloon guide of FIG. 1, particularly showing the attachment of the balloon to the guide body.

The present invention provides a single lumen balloon guide which is useful for a variety of procedures, such as coronary angioplasties. Referring in particular to the drawings, there is shown a balloon guide 10 constructed in accordance with a preferred embodiment of the present invention. Balloon guide 10 includes a guide body 11 comprised of a coiled wire 12 defining a cylindrical body having a central lumen 13 (FIG. 2). The coiled wire 12 may comprise a variety of suitable materials. Preferably the wire is a coiled, flat wire which is stiff enough to give the guide body good strength and stiffness and which permits the construction of a fairly small outside diameter for a reasonably large inside diameter without requiring the use of extremely fine or thin wire.

The central lumen 13 is open at the proximal and distal ends to permit fluid communication therethrough. A plug mandril 14 is extendable through the central lumen 13, and is operable to open or close the distal end of the central lumen in accordance with the operation of the present invention.

The coiled wire 12 includes two distinguishable portions. The wire includes a first, proximal portion 15 in which the coils are secured together with one another to inhibit their separation. This securement may be accomplished in a variety of suitable ways, with it being preferred that the first portion of the coiled wire be received within a cylindrical sleeve 16 (FIG. 2). The sleeve 16 preferably extends over the coiled wire from the proximal end of the coiled wire to the proximal end of the inflatable balloon 24. This sleeve 16 may comprise, for example, a polyethylene shrink tube that is supplied over the first portion of the coiled wire and reduced in size to snugly fit the coiled wire and thus hold the coils together.

The coiled wire 12 also includes a second, distal portion 17 in which the coils are normally adjacent (FIG. 2), but are separable from one another, as shown in FIG. 5. A pair of collars 18 and 19 are secured to the proximal and distal ends of the second portion 17. Since there are no restrictions as to separation of the coils in the portion 17 between the collars, the normally adjacent coils may be separated by an appropriate, external force. The separation of the coils in the second portion 17 is accomplished by the insertion of the plug mandril 14 through the central lumen 13 and against a stop, with further insertion causing the coiled wire 12 to be extended longitudinally, and the coils within the second portion 17 to separate.

The mandril and plug may be formed from a variety of materials. The mandril may, for example, be formed from stainless steel and may preferably be tapered in the direction of the distal end to provide varying flexibility of the mandril. The plug may similarly be formed from a variety of materials, and preferably is formed from vinyl. The shape and material of the plug 30 and the cannula 21 should be complementary to ensure a reliable seal when the plug is seated against the cannula.

Distal of the second portion 17, there is provided an additional portion 20 of the coiled wire 12. Secured, as by soldering, at the distal tip of the third portion 20, in which the wire coils are inseparable, is a cannula 21 (FIG. 5). The cannula 21 thereby provides a plug seat located within the central lumen 13 and distal of the second portion 17 of the coiled wire. This plug seat defines a passageway 22 communicating with the central lumen 13 and the distal opening 23 of the balloon guide. Closing off of the plug seat defined by cannula 21 therefore provides a closing off of the central lumen 13 and prevents fluid communication from the central lumen through the distal opening 23.

The guide body 11 further includes a balloon 24 attached to the coiled wire 12. The balloon is positioned over the second portion 17 of the coiled wire and is in fluid communication therewith. Thus, fluid passing from within the central lumen 13 and through the separated coils 17 (FIG. 5) will enter into and inflate the balloon 24.

Figure 3:
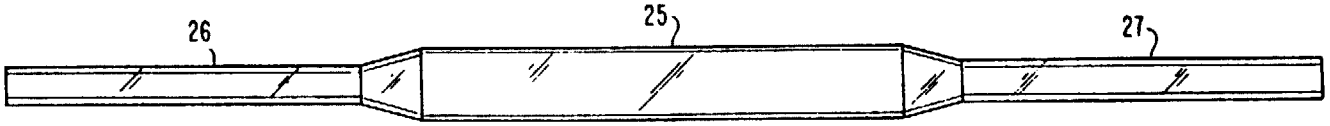
FIG. 3 is a plan view of a balloon used in connection with the balloon guide of the present invention.

The balloon 24 preferably includes a central balloon portion 25 (FIG. 3) and first and second sleeve extensions 26 and 27 extending therefrom. The first, proximal sleeve extension 26 is sealingly secured over the sleeve 16 received over the coiled wire 12. The second, distal sleeve extension 27 is received over the third portion 20 of the coiled wire 12. The second sleeve extension 27 operates in the same manner as the sleeve 16 and is sized to fit tightly about the third portion 20 of the coiled wire. Sleeve extension 27 thereby secures the coils together with one another and prevents separation of the coils in the third portion 20 of the coiled wire 12.

The guide body design of the present invention is adaptable to a variety of applications, and is sized accordingly. Procedures with which the balloon guide of the present invention could be used would include, but are not limited to, use as a coronary angioplasty catheter, an occlusion balloon catheter, a flow directed catheter, an infusion catheter, and the like. It would be apparent to those skilled in the art that appropriate changes or modifications to the design of the balloon guide could be made in order to adapt the guide to these and other types of uses and procedures.

A balloon guide useful for coronary angioplasty is described herein as exemplary of a preferred embodiment of the present invention. In this embodiment, the balloon guide preferably has an outside diameter of 0.038 inches (3 French) and an inside diameter of 0.0185–0.019 inches, and is useful with conventional wire guides up to 0.018 inches in outside diameter. Also for this application, the balloon diameter may range from 2 mm to 5 mm and the length may range from 1.0 to 5.0 centimeters. The balloon material would preferably comprise a clear, non-radiopaque, cross-linked polyethylene tubing having a wall thickness for the balloon portion of 0.001 inches to 0.005 inches. In the deflated condition, shown at 28 in FIG. 2, the balloon is flattened and folded circumferentially around the coiled wire in typical fashion. It will be appreciated, however, that modification to these and other design parameters may be adopted to render the balloon guide suitable for other applications.

The plug mandril 14 includes an elongated mandril 29 having proximal and distal ends. The plug mandril further includes a plug 30 secured to the distal end of the mandril. The mandril and plug sized to be receivable within the central lumen 13 of the guide body and extendable therethrough. The plug 30 defines a seating portion 31 sized and configured to be received against the plug seat of the guide body and to close off the plug seat when received thereagainst. Preferably, the plug 30 includes a tapered point 31 facing in the distal direction and defining the seating portion of the plug. This tapered point 31 is received against the proximal end of the cannula 21 in sealing relationship when the plug mandril is extended a sufficient distance within the central lumen of the guide body.

Referring in particular to FIGS. 5 and 6, the plug mandril 14 is shown in the position with the plug 30 seated against the cannula 21 and with the coils in the second portion 17 being separated to permit fluid communication therethrough. The plug mandril 14 also includes another position in which the plug 30 displaced proximally from the cannula. In this alternate position, the central lumen remains open through the distal opening 23, thus permitting fluid communication through the guide.

The plug mandril is extendable through the central lumen between the alternate positions with the plug 31 spaced from or seated against the cannula 21. Means are provided for positioning the plug mandril in each of the two alternate positions, and typically include a fitting 32 secured to the proximal end of the mandril 29.

Assembly 33 is secured to the proximal end of the guide body 11. Assembly 33 preferably includes a T-connector 34 to which is secured a collar 35. The collar is tapered in the distal direction and has a nose portion 36 to which is secured the proximal end of the guide body 11. The T-connector 34 defines a T-shaped passageway 37 communicating with the central lumen 13 of the guide body, and also with the balloon and mandril connectors 38 and 39, respectively. The balloon connector 38 has an outwardly extending flange 40 including threads 41 for reception of a balloon inflation device 42 in standard fashion.

The mandril connector 39 preferably includes an external thread upon which is threadedly received a locking connector 43. An O-ring 44 is positioned adjacent the end of the mandril connector 39 to provide a fluid tight seal between the locking connector 43 and mandril connector 39.

The fitting 32 on the plug mandril 14 is preferably configured to be lockingly and sealingly received by the locking connector 43. As shown particularly in FIG. 6, the locking connector includes an extension 45 having a series of circumferential ribs 46. The plug mandril fitting 32 includes a complementary extension 47 having a plurality of locking ribs 48. The respective extensions 45 and 47 are sized to be received one within the other with the locking ribs operating to engage the two together in a locked and sealing relationship. The plug mandril 13 includes a head 49 sealed within the fitting 32, as by epoxy 50, thus providing a secured and sealed connection between the plug mandril and fitting.

From the foregoing description, it will be apparent that the balloon guide of the present invention is operable between two alternate conditions to provide for fluid communication through the end opening 23 or to seal the end opening and provide for inflation or deflation of the balloon 24. In a first condition, the plug of the plug mandril is spaced apart from the cannula and fluid communication is available through the central lumen to the distal end 23. Such communication is available either through the balloon connector 38 or the locking connector 43, and may be used in a variety of procedures including for pressure measurements or for fluid infusion. If large volume injections are to be made, of if a small conventional type wire guide is to be used through the balloon guide, the plug mandril may be simply withdrawn out of the balloon guide.

In the alternate condition, the plug mandril is extended into and through the central lumen of the guide body to locate the plug 31 in sealing position against the plug seat of the cannula 21. Further, in this condition, the plug mandril is extended through the central lumen a sufficient distance to cause separation of the normally adjacent coils in the second portion 17 of the coiled wire 12. The plug mandril is preferably sized such that the appropriate positioning of the plug and stretching of the coiled wire is accomplished when the fitting 32 is received in the locked and sealed position connected with the locking connector 43. Thus, the plug mandril is pushed through the lumen and the fitting is positioned over the locking connector into the sealing relationship. In this condition, fluid communication through the distal end opening 23 is occluded by the plug. Moreover, fluid communication to the interior of balloon is available through the separated coil 17. In this condition, the balloon inflation device 42 may be operated to introduce fluid into and through the central lumen and through the separated coils of the second portion 17 for inflating the balloon. Conversely, fluid may be withdrawn from the interior of the balloon 24 in order to deflate the balloon when the balloon guide is in this condition.

Referring in particular to FIG. 7, there is shown an alternate design for a plug mandril useful with the present invention. Plug mandril 51 includes a mandril 52 and a plug 53 attached to the distal end thereof. As shown in FIG. 7, the mandril 52 may comprise simply a more conventional wire guide without the distal taper as shown in the embodiment of FIG. 4. Attached to the distal end of the plug 53 is a wire 54 and wire guide 55. The wire 54 and guide 55 may comprise a variety of suitable configurations, including a typical coiled wire as shown for the guide 55. These components are sized to fit through the cannula 21 and to extend out through the distal end opening 23 when the plug 53 is seated in the sealing position against the cannula 21 in the same fashion as shown in FIG. 5. This alternate design for the plug mandril 51 enables the user of the balloon guide to manipulate the balloon guide with a wire guide extending beyond its tip, while still being able to plug the central lumen of the balloon guide for balloon inflation while the wire guide extends therefrom. This alternate configuration may be necessary occasionally to anchor the balloon guide in place while inflating the balloon.

The balloon 24 may be formed in any of a variety of known techniques, such as by blow molding. Attachment of the balloon may be accomplished by heat bonding the balloon to the shrink tube 16 and also by heat shrinking the distal extension 27 to the coiled wire 20. Other shapes and compositions of balloon may alternately be used to adapt the balloon guide for the variety of other procedures with which it would be useful. The use of a small latex balloon, for example, would make the guide suitable as an occlusion balloon catheter or the like.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A balloon guide which comprises:

a guide body comprising a coiled wire forming a cylindrical body having a central lumen open at the proximal and distal ends, said coiled wire including a first, proximal portion in which the coils are secured together with one another, and a second, distal portion in which the coils are normally adjacent one another but are separate from one another, said guide body including a plug seat located within the central lumen distal of the second portion of the coiled wire, the plug seat defining a passageway communicating with the central lumen, the plug seat being configured to provide a closing off of the central lumen upon closing off of the plug seat, said guide body further including a balloon attached to the coiled wire, the balloon being positioned over and in fluid communication with the second portion of the coiled wire to enable fluid passing from within the central lumen and through the separated coils of the second portion to enter into and inflate the balloon;

a plug mandril comprising an elongated mandril having proximal and distal ends, said plug mandril further including a plug secured to the distal end of the mandril, the mandril and plug being sized to be receivable within the central lumen of said guide body and extendable therethrough, the plug defining a seating portion sized and configured to be received against the plug seat of said guide body and to close off the plug seat when received thereagainst;

extension means for extending said plug mandril into and through the central lumen of said guide body between first and second positions, the first position locating the plug of the mandril spaced from the plug seat of said guide body to permit fluid communication through the plug seat, the second position locating the plug in sealing position against the plug seat and preventing fluid communication therethrough, said extension means extending said plug mandril in the second position through the central lumen a sufficient distance to cause separation of the normally adjacent coils in the second portion of the coiled wire; and inflation means communicating with the central lumen of said guide body for introducing a fluid into the central lumen and through the separated coils of the second portion of the coiled wire for inflating the balloon when said plug mandril is in the second position within the guide body.

2. The balloon guide of claim 1 in which the coiled wire of said guide body is a flat wire.

3. The balloon guide of claim 1 in which said guide body includes a cannula member positioned within the central lumen and defining the plug seat.

4. The balloon guide of claim 1 in which the plug of said plug mandril includes a tapered point facing in the distal direction and defining the seating portion of the plug.

5. The balloon guide of claim 4 in which said guide body includes a cannula member positioned within the central lumen and defining the plug seat, the tapered point of the plug being received against the cannula member in sealing relationship with the plug mandril in the second position.

6. The balloon guide of claim 1 in which said guide body includes a sleeve received over the first portion of the coiled wire, the sleeve being sized to fit tightly about the first portion of the coiled wire and securing the coils together with one another and preventing separation thereof.

7. The balloon guide of claim 6 in which said guide body includes a sleeve extending over the coiled wire from the proximal end of the coiled wire to the proximal end of the balloon.

8. The balloon guide of claim 7 in which said guide body includes a third portion of coiled wire distal of the second, separable portion, the balloon of said guide body includes a central balloon portion and first and second sleeve extensions therefrom, the first sleeve extension being proximal of the central balloon portion and being sealingly secured over the sleeve received over the coiled wire, the second sleeve extension being distal of the central balloon portion and being received over the third portion of coiled wire, the second sleeve extension being sized to fit tightly about the third portion of the coiled wire and securing the coils together with one another and preventing separation thereof.

9. The balloon guide of claim 6 in which the coiled wire of said guide body is a flat wire.

10. The balloon guide of claim 1 and which further includes locking means for locking said plug mandril in the second position relative said guide body.

11. The balloon guide of claim 10 in which said guide body includes a sleeve received over the first portion of the coiled wire, the sleeve being sized to fit tightly about the first portion of the coiled wire and securing the coils together with one another and preventing separation thereof.

12. The balloon guide of claim 10 in which the coiled wire of said guide body is a flat wire.

13. The balloon guide of claim 12 in which said guide body includes a sleeve received over the first portion of the coiled wire, the sleeve being sized to fit tightly about the first portion of the coiled wire and securing the coils together with one another and preventing separation thereof.

14. The balloon guide of claim 13 in which said guide body includes a cannula member positioned within the central lumen and defining the plug seat.

15. The balloon guide of claim 13 in which the plug of said plug mandril includes a tapered point facing in the distal direction and defining the seating portion of the plug.

16. The balloon guide of claim 15 in which said guide body includes a cannula member positioned within the central lumen and defining the plug seat, the tapered point of the plug being received against the cannula member in sealing relationship with the plug mandril in the second position.

17. A method for inflating a balloon guide which comprises the steps of:

a. providing a guide body having a coiled wire forming a cylindrical body having a central lumen open at the proximal and distal ends, the guide body including a first portion of the coiled wire in which the coils are secured together with one another, and a second portion of the coiled wire in which the coils are normally adjacent one another but are separable from one another, the guide body including a plug seat located within the central lumen distal of the second portion of the coiled wire, the plug seat defining a passageway communicating with the central lumen, the plug seat being configured to provide a closing off of the central lumen upon closing off of the plug seat, the guide body further including a balloon attached to the coiled wire and positioned over the second portion of the coiled wire to enable fluid passing from within the central lumen and through the separated coils of the second portion to enter into and inflate the balloon;

b. providing a plug mandril comprising an elongated mandril having proximal and distal ends, the plug mandril further including a plug secured to the distal end of the mandril, the mandril and plug being sized to be receivable within the central lumen of said guide body and extendable therethrough, the plug defining a seating portion sized and configured to be received against the plug seat of said guide body and to close off the plug seat when received thereagainst;

c. extending the plug mandril into and through the central lumen of said guide body to locate the plug in sealing position against the plug seat and a sufficient distance to cause separation of the normally adjacent coils in the second portion of the coiled wire; and d. after step c., introducing a fluid into the central lumen and through the separated coils of the second portion of the coiled wire for inflating the balloon.

*18. The balloon guide of claim 1, wherein said plug mandril further includes a wire guide attached to said plug portion and extending distally therefrom, said wire guide being of sufficient length to extend beyond said distal end of said guide body when said plug portion is received against said plug seat.*

*19. A balloon guide comprising:*

*a guide body having an elongated cylindrical body, a proximal end, a distal end, and a central lumen therethrough open at said proximal end and said distal end, said guide body having a plug seat adjacent said distal end, and at least part of said guide body between said proximal end and said plug seat being formed of a plurality of coils, said coils being separable from a normal position;*

*a balloon attached to said guide body between said proximal end and said plug seat with said plug seat distal said balloon, said balloon positioned over and in fluid communication with at least a portion of said plurality of coils to enable fluid passing from within said central lumen and through said coils to enter into and inflate the balloon; and*

*a plug mandril having an elongated body portion and a plug portion, said plug mandril sized to be receivable through said central lumen and extendable through said lumen and said balloon to engage said plug seat, said plug portion being sized and configured to close said central lumen at said distal end of said guide body when pressed against said plug seat; and*

*means for separating said plurality of coils from said normal position,*

*said balloon being inflatable by forcing fluid into said central lumen while pressing said plug portion of said plug mandril against said plug seat to close said central lumen at said plug seat with the fluid passing through said central lumen and between said plurality of coils, with said plurality of coils separated, into said balloon to inflate said balloon.*

*20. The balloon guide of claim 19 wherein,*

*said plug mandril further includes a wire guide attached to said plug portion and extending distally therefrom, said wire guide being of sufficient length to extend significantly beyond said distal end of said guide body when said plug portion is pressed against said plug seat.*

*21. A method of performing a medical procedure for expansion of a balloon within a vessel comprising the steps of:*

*providing a balloon guide including a guide body having an elongated cylindrical body and a central lumen therethrough open at the proximal and distal ends of the body, the guide body having a plug seat adjacent the distal end, and at least part of the guide body adjacent the plug seat being formed of a plurality of coils, the balloon guide further including a balloon attached to the guide body between the proximal end and the plug seat with the plug seat distal the balloon, the balloon covering at least a portion of the plurality of coils, the balloon guide also including a plug mandril having an elongated body portion and a plug portion, the plug mandril having a diameter capable of passing freely through the central lumen to the*

*distal end, the plug portion being capable of closing the central lumen when pressed against the plug seat;*

*guiding the balloon guide to a desired location within a patient;*

*pressing the plug mandril against the plug seat thereby closing the central lumen of the guide body distally of the balloon;*

*forcing fluid into the central lumen at the proximal end of the guide body and between the plurality of coils into the balloon, thereby inflating the balloon;*

*deflating the balloon; and*

*withdrawing the balloon guide from the patient.*

*22. The method of claim 21 wherein,*

*said balloon guide is used as a coronary angioplasty balloon.*

*23. The method of claim 21 wherein,*

*said balloon guide is used as an occlusion balloon catheter.*

*24. The method of claim 21 wherein,*

*said balloon guide is used as a flow directed catheter during said step of guiding the balloon guide.*

*25. The method of claim 21 wherein,*

*said balloon guide is used as an infusion catheter.*

*26. The method of claim 21 further comprising:*

*infusing radiopaque liquid through the central lumen and out the distal end of the balloon guide into the patient.*

*27. The method of claim 21 further comprising:*

*taking pressure measurements from within the patient via fluid communication between the distal and proximal ends of the guide body.*

*28. The method of claim 21 wherein,*

*said step of deflating the balloon is accomplished by withdrawing the fluid from the guide body.*

*29. The method of claim 21 wherein,*

*said plug mandril further includes a wire guide attached to said plug portion and extending distally therefrom, said wire guide being positioned to extend beyond the distal end of the guide body; and the method further comprises:*

*anchoring the distal end of the balloon guide at the desired location within the patient with said wire guide.*

*30. A balloon guide comprising:*

*a guide body including:*

*a cylindrical body having a central lumen open at the proximal and distal ends of said body, said cylindrical body including a distal portion formed of a plurality of coils, said coils being separable from a normal position; and*

*a plug seat located within said central lumen at said distal end of said guide body, said plug seat defining a passageway communicating with said central lumen and being configured to provide a closing off of said central lumen upon closing off of said plug seat;*

*a balloon attached to said guide body between said proximal end and said plug seat with said plug seat distal said balloon, said balloon being positioned over and in fluid communication with said plurality of coils to enable fluid passing from within said central lumen and through said coils to enter into and inflate said balloon;*

*a plug mandril sized to be receivable within and extendable through said central lumen of said guide body and including an elongated mandril having proximal and distal ends, and a plug portion secured to said distal end of said mandril, said plug portion defining a seating portion sized and configured to be received against said plug seat of said guide body to close off said plug seat when received thereagainst; and*

*extension means for extending said plug mandril into and through said central lumen from said proximal end to said distal end of said guide body between first and second positions, said first position locating said plug portion spaced from said plug seat of said guide body to permit fluid communication through said passageway of said plug seat, and said second position locating said plug portion in sealing position against said plug seat and preventing fluid communication therethrough, said extension means extending said plug mandril in said second position through said central lumen a sufficient distance to cause separation of said plurality of coils from said normal position.*

* * * * *